US006410597B1

(12) United States Patent
Bieberich et al.

(10) Patent No.: US 6,410,597 B1
(45) Date of Patent: Jun. 25, 2002

(54) HYDROXYALKYL AMIDE ANALOGS OF CERAMIDE

(75) Inventors: Erhard Bieberich, Richmond; Raphael M. Ottenbrite, Midlothian; Robert K. Yu, Richmond; Helen Fillmore, Richmond; William C. Broaddus, Richmond, all of VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/512,597

(22) Filed: Feb. 25, 2000

(51) Int. Cl.$^7$ .................. A61K 31/16; A61K 31/045
(52) U.S. Cl. .................. 514/625; 514/613; 514/627; 514/629; 514/630; 514/727; 514/730; 514/738; 514/739
(58) Field of Search .................. 514/613, 629, 514/627, 630, 727, 738, 739, 730

(56) References Cited

U.S. PATENT DOCUMENTS

| 3,883,661 A | * | 5/1975 | Young ................. 514/325 |
| 4,822,605 A | * | 4/1989 | Powell ................ 424/85.2 |
| 5,231,087 A | * | 7/1993 | Thornfeldt ............. 514/53 |
| 5,583,088 A | * | 12/1996 | Kawamura ............. 503/205 |

FOREIGN PATENT DOCUMENTS

| EP | 0 804 179 B1 | * | 7/1999 |
| WO | WO-95/21175 A1 | * | 8/1995 |
| WO | WO-96/18391 A2 | * | 6/1996 |

OTHER PUBLICATIONS

STN/CAS online, file Registry, Kita et al., JP 09003018 (1997), Abstract.*

Schwarz et al., 'Anadamide, an endogenous cannabinoid receptor agonist inhibits lymphocyte proliferation and induces apoptosis', Journal of Neuroimmunology (1994), vol. 55, pp. 107–115.*

Mazzari et al., 'N–(2–Hydroxyethyl) hexadecanamide is orally active in reducing edema formation and inflammatory hyperalgesia by down–modulating mast cell activation', European Journal of Pharmacology (19960), vol. 300, pp. 227–236.*

Garg et al.,'An antiviral sphingosine derivative from the green alga Ulva Fasciata', Tetrahedron Letters (1992), vol. 33, No. 12, pp. 1641–1644.*

STN/CAS online, file HCAPLUS, Acc. No. 1976:99474, Doc. No. 84:99474, (Svec et al., Neoplasma (1975), 22 (6), pp. 625–630), Abstract.*

Petrocellis et al.,'Anandamide, an endogenous cannabinomimetic substance, modulates rat brain protein kinase C in vitro', Biochemistry and Molecular Biology International (1995), vol. 36, No. 6, pp. 1127–1133.*

Petrocellis et al., 'The endogenous cannabinoid anandamide inhibits human breast cancer cell proliferation', Proc. Natl. Acad. Sci. USA (1998), vol. 95, pp. 8375–8380.*

STN/CAS online, file HCAPLUS, Acc. No. 1996:464360, Doc. No. 125:105139, (Ito, JP 08113535 A2 (1996)), Abstract.*

STN/CAS online, file HCAPLUS, Acc. No. 1996:470549, Doc. No. 125:216457, (Sharma et al., Bot. Mar. (1996), 39 (3), pp. 213–215), Abstract.*

* cited by examiner

Primary Examiner—Jose' G. Dees
Assistant Examiner—Frank Choi
(74) Attorney, Agent, or Firm—Whithan, Curtis & Christofferson, P.C.

(57) ABSTRACT

The present invention provides methods for treating disease conditions associated with abnormal cellular proliferation, inflammation and viral infection or proliferation by the administration of ceramic analogs. The ceramic analogs appear to be specific for modulation of the enzyme PKCζ.

4 Claims, 9 Drawing Sheets

HYDROXYALKYL AMIDE ANALOGS OF CERAMIDE

This invention was made using funds from grants from the National Institutes of Health having grant number NSF 11853. The government may have certain rights in this invention.

BACKGROUND OF THE INVENTION

1. Field of the Invention

The invention generally relates to hydroxy alkyl amide analogs of ceramic and their use in the treatment of pathological conditions or disorders caused by abnormal cell growth, inflammatory processes, virus proliferation and processes involving aberrant protein kinase C ζ (PKCζ) activity. The invention also relates to the use of hydroxy alkyl amide analogs of ceramic for analysis and diagnostic evaluation of 1) the enzyme PKCζ and 2) programmed cell death (apoptosis), both in vitro and in vivo.

2. Background of the Invention

Figure 1A:
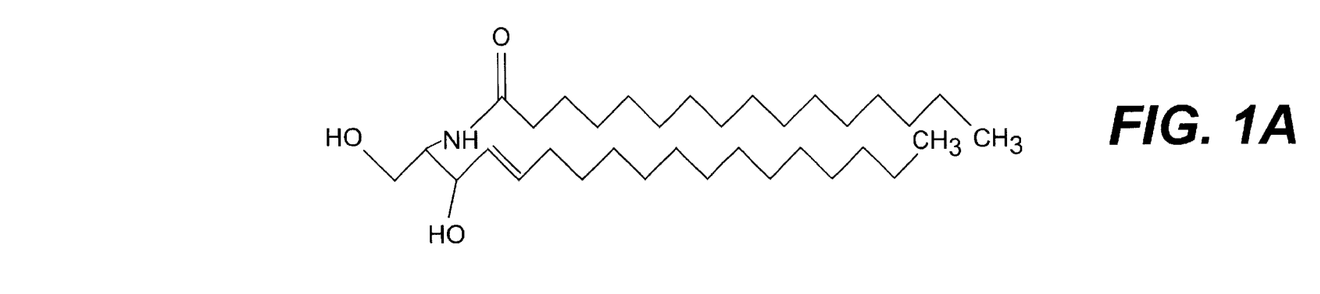
FIGS. 1A, 1B, and 1C. Chemical structures of: ceramic (1A); N-palmitoyl serinol or "S16" (1B), and N-oleoyl serinol or "S18" (1C).

Sphingosine and its N-acylated derivative, ceramic (FIG. 1) are important lipid second messengers for regulation of cell growth and apoptosis (programmed cell death), as well as functioning as entry substrates for the generation of phospho-and glycosphingolipids. In particluar, apoptosis is known to be induced by elevation of endogenous ceramic or sphingosine (Ariga et al. 1998; Hannun and Linardic, 1993). Occasionally, cell growth and apoptosis share intracellular signal transduction by common protein kinase cascades. It is well known that apoptosis causes the death of half of the mitotic neuronal or glial cells during early periods of nervous system development (Mangoura and Dawson, 1998). Furthermore, spontaneous regression of astrocytoma tumors in young children has been correlated with an apoptotic process in rapidly dividing cells (Schwab, 1999).

Cerarnide specifically activates a protein kinase (ceramic activated protein kinase) and a phosphatase (ceramic activated phosphatase), both of which are known to participate in apoptotic or mitogenic signal transduction pathways (Ariga et al., 1998; Hannun and Linardic, 1993). Recently, a second protein kinase, protein kinase C zeta (PKCζ), has been reported to be regulated by ceramic and to constitute an important switch for mitosis versus apoptosis (Muller et al., 1995). Interestingly, in in vitro assays, it has been shown that the regulation is dependent on the effector concentration, in that PKCζ appears to be activated at low concentrations of ceramic and inhibited at high concentrations of ceramic.

Structural analogues of ceramic are expected to specifically target sphingolipid-binding enzymes by acting as potential inhibitors or allosteric effectors. Ceramic analogues which are currently commercially available however, function only either as inhibitors of glycosphingolipid biosynthesis or ceramic degradation, in both cases giving rise to an elevation of endogenous ceramic. Two out of six enzymes critical for ceramic metabolism have been reported to be inhibited by structural analogues of ceramic. D-threo-1-phenyl-2-decanoylamino-3-morpholino-1-propanol (d-threo-PDMP) and related derivatives are known to inhibit glycosyl transferase (GT) whereas d-erythro-2-(N-myristoylamino)-1-phenyl-1-propanol (d-erythro-MAPP) and N-oleoyl ethanolamine (NOE) are used for inhibition of ceramidase (Abe et al., 1995; Arora and Radin, 1972; Bielawska et al., 1996). PDMP has been suggested for treatment of cancer by elevation of endogenous ceramic (see, for example, U.S. Pat. Nos. 5,952,370 and 5,041,441 to Shayman et al.). However, it has been reported that this ceramic analogue has detrimental side effects on the appearance and morphology of cultured neuroblastoma cells, and that it elevates ceramic in resting but not in rapidly dividing cells (Bieberich et al., 1999). Furthermore, a direct binding to distinct protein kinases involved in the regulation of apoptosis (e.g. PKCζ) has not been demonstrated.

Activity of PKCζ has been implicated in: several types of cancer (e.g. colon, rectal, prostate, leukemia, etc.) (Hochegger et al., 1999; Powell et al., 1996; and Ways et al., 1994); infection by and proliferation of several types of viruses (e.g. Sendai, parainfluenza, HIV, etc.), (De et al., 1995; and Folgueira et al., 1996; Huntley et al., 1997); cell signaling in inflammatory processes (Jordan et al. 1996; MacDonald et al., 1999); and proliferation of epidermal and airway smooth muscle cells (Mani et al, 1999; Carlin et al, 1999; Das et al., 2000). In addition, aberrant activity of PKCζ has also been implicated in the etiology of Alzheimer's disease (Moore et al, 1998). The involvement of PKCζ in these processes suggests that modulation of this enzyme may provide a means of treating related disease conditions.

SUMMARY OF THE INVENTION

It would be highly desirable to have available novel analogues of ceramic with high binding specificity for protein kinases (e.g. PKCζ) that are involved in the regulation of cell growth, differentiation, and apoptosis. It would be highly desirable to have available methods for administering such compounds in order to ameliorate disease conditions associated with regulation of cell growth, differentiation, and apoptosis. It would be highly desirable to have available compounds and methods of administering compounds which induce apoptosis specifically in rapidly dividing cells.

The present invention provides novel hydroxy alkyl amide compounds depicted in Formula I which are analogs of ceramic. The invention also provides methods of use for hydroxy alkyl amide compounds (depicted in Formula I and Formula II) which are analogs of ceramic to treat diseases associated with abnormal cell proliferation, inflammation and viral infection. The invention also provides methods for modulating the activity of the enzyme protein kinase Cζ (PKCζ). The invention further provides methods for inducing apoptosis in cells both in vivo and in vitro.

DETAILED DESCRIPTION OF THE PREFERRED EMBODIMENTS OF THE INVENTION

The present invention provides methods for the therapeutic use of N-acylated hydroxy alkyl amide analogs of ceramic for the treatment of disease conditions associated with abnormal cell proliferation, inflammatory processes, and viral infection and proliferation. The compounds utilized in the methods of the present invention display several advantages over ceramic itself, or other known analogs thereof. For example, they display high aqueous solubility and no or low toxicity in in vivo animal models. The compounds may be produced in a relatively straightforward and cost effective manner. Further, because they appear to specifically modulate the enzyme PKCζ, the consequences of their use is more defined, simplifying the analysis of their clinical applications.

It is known that other ceramic analogs have detrimental side effects on the appearance an morphology of cultured cells, in particular when the cells are resting and not propagating (Bieberich et al. 1999). An advantage of the compounds utilized in the present invention is that they are specifically active on rapidly dividing cells whereas resting or differentiated cells remain unaffected (Bieberich et al., 2000). By "rapidly dividing cells" we mean cells which are in logarithmic phase of growth rate (e.g. 30–70% confluent cells in vitro).

Without being bound by theory, the compounds utilized in the practice of the present invention appear to exert their effect by modulating the activity of the enzyme PKCζ. The compounds used in the practice of the present invention have been shown to be specific modulators of PKCζ. They therefore may be useful for the treatment of any disease condition associated with PKCζ. By "associated with" we mean disease conditions which result from or are in part mediated by aberrant (i.e. abnormal) activity of PKCζ. Such conditions may be the result of abnormal expression of the gene which encodes the enzyme (e.g. either over- or under-expression); of the expression of an abnormal form of the gene (e.g. deletion, substitution, and insertion mutations, or variant forms of the enzyme that result from alternative splicing, or any form of post-translational modification of the enzyme); or of abnormal levels of enzyme activity due to the presence or absence of inhibitors or activators, or for any other reason. Any conditions which result from an abnormal level of activity of the enzyme PKCζ may be treated by the methods of the present invention.

By "modulate" the activity of PKCζ, we refer to the observation that the compounds utilized in the methods of the present invention conditionally activate or inhibit PKCζ, depending on the compound concentration or the presence or absence of additional effectors.

By disease conditions, we mean any condition in which the reversal thereof would be considered to be in the best interest of the health and comfort of the patient, including but not limited to so-called life threatening diseases e.g. cancer, and also much milder conditions such as non-life-threatening but unsightly skin disorders which result from, for example, the over-proliferation or inflammation of cells, e.g. psoriasis.

In one preferred embodiment of the present invention, the disease condition which is treated by the practice of the methods of the present invention is associated with abnormal cell proliferation. Examples of such conditions which may be treated include but are not limited to: cancer (for example, prostate, colon, rectal, breast, leukemia, brain, etc.) and aberrant epidermal or fibroblast proliferation (e.g. in hypoxia-induced pulmonary hypertension). Any disease associated with abnormal cellular proliferation which is amenable to treatment using the methods of the present invention may be treated by the practice of the present invention.

In another preferred embodiment of the present invention, the disease condition which is treated by the practice of the methods of the present invention is associated with viral infection and proliferation. Examples of such conditions include but are not limited to those associated with HIV, Sendai and parainfluenza viruses. Any disease associated with viral infection and proliferation which is amenable to treatment using the methods of the present invention may be treated by practice of the present invention.

In yet another preferred embodiment of the present invention, the disease condition which is treated by the practice of the methods of the present invention is associated with inflammatory processes. Examples of such conditions include but are not limited to inflammatory processes involved in arthritis and neurodegeneration, e.g. by aging or chronic HIV-1 infection. Any disease associated inflammatory processes which is amenable to treatment using the methods of the present invention may be treated by practice of the present invention.

In yet another preferred embodiment of the present invention, the disease condition which may be treated by the methods of the present invention is associated with pathological condition or disease processes associated with an aberrant activity of PKCζ. Examples or such conditions include but are not limited to the etiology of Alzheimer's disease. Any disease associated with an aberrant (i.e. abnormal) activity of PKCζ may be treated by the practice of the present invention.

The present invention provides novel compounds for use in the treatment of diseases associated with abnormal cell proliferation, inflammatory processes, and viral infection and proliferation. Further, the novel compounds may be used to treat any disease condition associated with the enzyme PKCζ. The general structure of the novel compounds is depicted in Formula I, wherein R=a saturated or mono- or polyunsaturated (cis or trans) alkyl group having greater than 5 carbon atoms (most preferably 12–20 carbon atoms); R1, R2 and R3 may be the same or different and are hydroxylated alkyl groups (e.g. hydroxymethyl or hydroxyethyl) or hydrogen; and R4 is hydrogen, an alkyl chain having from 2 to 12 carbon atoms, or an aryl moiety (e.g. benzyl or tolyl). (Serinol is not considered a "new compound" within this invention but its novel applications discussed below would be new and useful.) In a preferred embodiment of the present invention, the hydroxylated alkyl groups have from 1–5 carbon atoms.

FORMULA I

Those of skill in the art will recognize that many variations of the novel compounds of Formula I exist, and all such variations are encompassed by the present invention.

The present invention provides methods for the treatment of disease conditions associated with abnormal cell proliferation, inflammation and viral infection. The methods encompass the administration of compounds of the general formula depicted in:
1) Formula I as described above, or
2) Formula II, below, wherein R=a saturated or mono- or polyunsaturated (cis or trans) alkyl group having greater than 5 carbon atoms; and R1 and R2 may be the same or different and are hydroxylated alkyl groups or hydrogen. In one preferred embodiment of the methods of present invention, R of Formula II is a saturated or unsaturated alkyl group having from 12–20 carbon atoms. In another preferred embodiment of the methods of the present invention, the hydroxylated alkyl groups of Formula II have from 1–5 carbon atoms.

FORMULA II

Figure 1B:
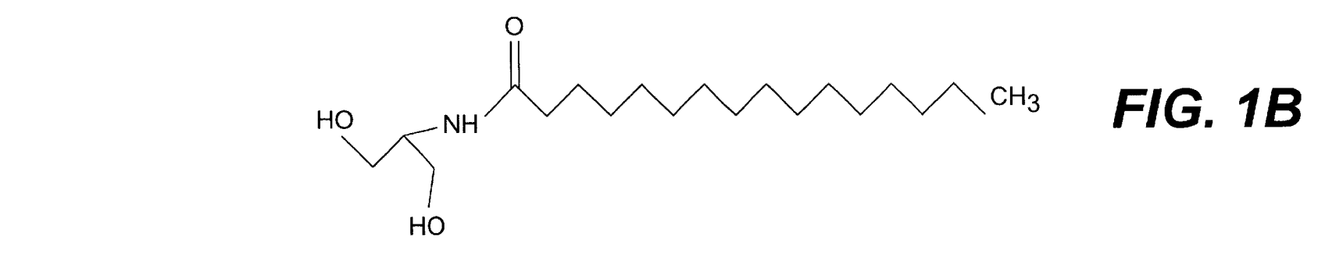
Figure 1C:
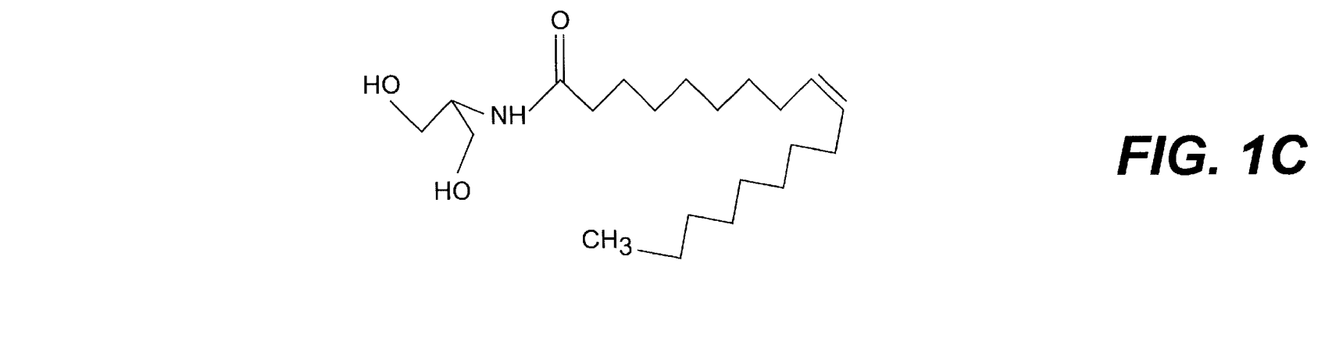
Figure 2A:
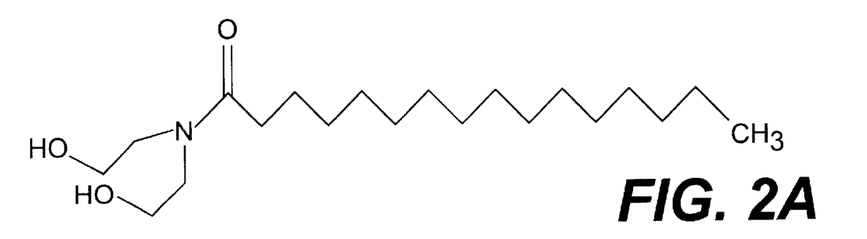
FIGS. 2A, 2B, 2C and 2D. Chemical structures of: N,N-bis(2-hydroxyethyl) palmitamide or "B16" (2A); N,N-bis(2-hydroxyethyl)oleamide or "B18" (2B); N-[tris (hydroxymethyl)methyl]palmitamide or "T16" (2C); and N-[tris(hydroxymethyl)methyl]oleamide or "T18" (2D).
Figure 2B:
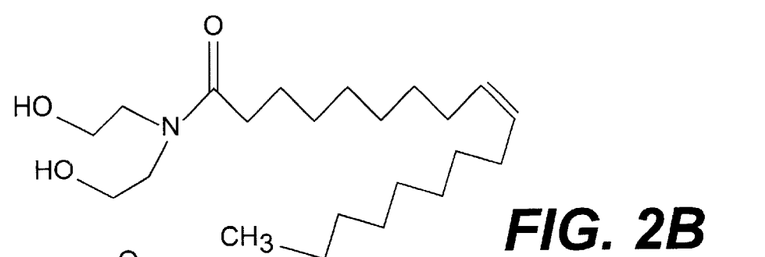
Figure 2C:
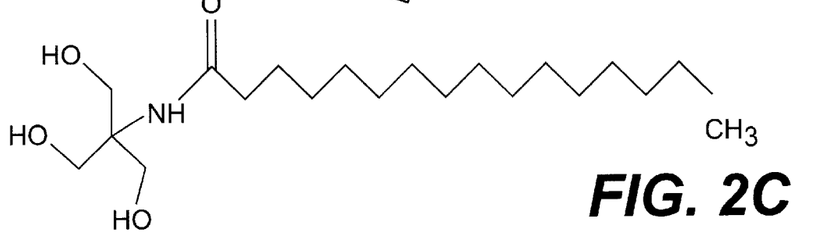
Figure 2D:
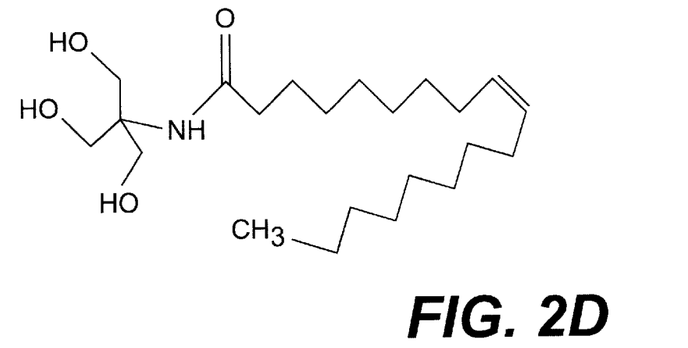

In preferred embodiments of the present invention, the methods of the present invention utilize the following compounds: N-palmitoyl serinol or "S16" (FIG. 1B), N-oleoyl serinol or "S18" (FIG. 1C), N,N-bis(2-hydroxyethyl) palmitamide or B16 (FIG. 2A), N,N-bis(2-hydroxyethyl) oleamide "B 18" (FIG. 2B), N-[tris(hydroxymethyl)methyl] palmitamide "T16" (FIG. 2C) and N-[tris(hydroxymethyl) methyl]oleamide or T18" (FIG. 2D). Those of skill in the art will recognize that many other variations of Formulas I and II exist, and the use of all such variations is encompassed by the methods of the present invention.

Those of skill in the art will recognize that the compounds used in the practice of the present invention may be employed in a wide variety of pharmaceutical forms. They may be employed neat or admixed with pharmaceutically acceptable carriers, excipients, additives, preservatives, buffers, and the like. Therapeutically acceptable salts of the compounds may be employed.

Generally speaking, the compounds will be administered orally, intravenously, or by direct infusion to tissues. However, any therapeutically acceptable method of administration may be employed in the practice of the present invention.

The selection of dosage, rate/frequency and means of administration is well within the skill of the artisan and may be left to the judgment of the treating physician or veterinarian. However, in general the dosage range of about 20–50 mg/kg of body or tissue weight is likely. The method of the present invention may be practiced alone or in conjunction with other therapeutic regimens, for example, radiation or chemotherapy regimens.

Those of skill in the art will also recognize that the methods of the present invention and the novel compounds of the present invention may be useful as investigational or diagnostic tool. The enzyme PKCζ plays a pivotal role in cell signaling. Methods which utilize compounds that specifically modulate the enzyme may be useful in laboratory settings for the investigation of phenomena related to cell signaling, such as cellular proliferation, differentiation, and programmed cell death. Those of skill in the art will recognize that, in general, compounds which specifically modulate an enzyme are very useful for investigating the enzyme in a variety of ways. For example, the ceramic analogs utilized in the present invention may be utilized as inducers of apoptosis in in vitro cell culture systems. Further, the ceramic analogs utilized in the present invention may be immobilized and used for affinity chromatography in order to isolate biological macromolecules which bind to the compounds.

EXAMPLES

Methods

Cell lines

Murine neuroblastoma x rat glioma NG108-15 and murine neuroblastoma x rat dorsal root ganglion F-11 cells were kindly provided by Drs. Robert Ledeen (New Jersey School of Medicine, Newark, N.J.) and Glyn Dawson (University of Chicago, Chicago, Ill.), respectively. PC12 (rat adrenal pheochromocytoma, ATCC CRL 1721) cells were purchased from the American Type Culture Collection (Manassas, Va.). U87 and T98 human glioma cells were purchased from the American Type Culture Collection (Manassas, Va.). RT2 rat glioma cells were a gift.

Synthesis of compounds

The compound S16 (2-palmitoyl-1,3-propanediol) was synthesized from a solution of 50 mg (549 μmoles) of 2-amino-1,3-propanediol in 15 ml of pyridine supplemented with 1.65 mmol (457 μl) of palmitoylchloride at −30° C. The reaction mixture was stirred for 2 hours at room temperature followed by the addition of 30 ml of CH$_3$OH. After stirring for another 2 hours at room temperature the reaction mixture was concentrated by evaporation. For selective hydrolysis of any ester groups formed during the reaction, the concentrate was treated with a 30 ml solution of CH$_3$OH and sodium methoxide (pH 11–12) and stirred for 2 hours at room temperature. The reaction mixture was neutralized with dilute HCl and then concentrated. The reaction product obtained was purified by chromatography on a silica gel column (5 g) with CHCl$_3$/CH$_3$OH (5:1 by volume) as the eluent. The yield of S16 was 135 mg (75%). The purity and structure were verified by nuclear magnetic resonance (NMR) and mass spectrometry.

The octanoyl-, oleoyl-, and stearoyl derviatives S8, S18 and SS18) were synthesized following the procedure used above for the synthesis of S16, but using octanoyl chloride, oleoyl chloride and stearoyl chloride, respectively, instead of palmitoyl chloride in the procedure.

The T16 was prepared by following the procedure used above for the synthesis of S16, but using bis(hydroxyethyl) amine instead of 2-amino-1,3-propanediol. The T18 was prepared by following the procedure used above for the synthesis of T16, but using oleoyl chloride instead of palmitoyl chloride in the procedure.

Synthesis of S16 Affinity Gel

Octyl Sepharose 4B™ (Fast Flow™ Pharmacia), 2 ml, was washed 3 times with 10 ml of CH$_3$OH/0.1 M KCl (1:1 volume) and then 3 times with 10 ml of solvent A (CHCl$_3$/ CH$_3$OH/H$_2$O, 30:60:8 by volume). The Sepharose gel (2 ml)

was supplemented with 2 ml of solvent A containing 4 mg of S16 and incubated for 30 min at room temperature. The gel was then washed with 10 ml of $CH_3OH/PBS$ (1:1 by volume) and 10 ml of phosphate buffered saline (PBS), respectively, before use.

High Performance Thin Layer Chromatography (HPTLC)

Lipids were prepared and analyzed by HPTLC as described previously (Freischutz et al., 1997).

Analysis of Apoptosis and General Methods

Apoptosis was analyzed by DNA fragmentation, in situ terminal nucleotidyl transferase assay, and staining of condensed chromatin with Hoechst dye 33258 as described elsewhere (Ji et al., 1995; Bieberich et al., 1999) and as further outlined below. The degree of cell death was monitored by determination of the number of floating cells and cells stained with 0.4% trypan blue (Wang et al., 1999).

Dependence of S16 induced apoptosis of NG108-15 cells on cell density

Cells were grown to varying degrees of confluence ($100\%=1.0\times10^5$ $cells/cm^2$) and then incubated overnight with 100 $\mu$M S16. The floating cells were harvested from the medium and the amount of cellular protein determined for calculation of dead cells. In addition, cell death was quantified by staining with trypan blue. The attached cells were stained with Hoechst dye 33258 for calculation of apoptotic cells with condensed chromatin. The number of apoptotic cells was determined by counting 100 stained cells in 20 different areas on tissue culture dishes from three independent experiments.

Dependence of apoptosis on cell cycle

The dependence of apoptosis on cell cycle was analyzed by detection of cyclin E using a specific antibody for immunofluorescence microscopy. Apoptotic cells were stained with Hoechst dye or identified by terminal nucleotidyl transferase assay.

Dependence of apoptosis on cell differentiation

The dependence of apoptosis upon differentiation of cells was analyzed by incubating undifferentiated PC12 cells and PC12 cells which had been induced to differentiate with S16 for 24 hours. Differentiation was induced by preincubation with 10 $\mu$M forskolin for 48 hrs. The extent of apoptosis was determined by staining with Hoechst dye 33258.

Effect of alkyl chain length on apoptotic potential of N-acylated compounds

Neuroblastoma cells (NG108-15 or F-11) were grown to 30% confluence and incubated overnight with various concentrations of N-acyl compounds containing carbon chains with 8, 16 and 18 carbons, as well as C16 ethanolamine. The floating cells were harvested from the medium and the amount of cellular protein determined for calculation of dead cells. In addition, cell death was quantified by staining with trypan blue. The attached cells were stained with Hoechst dye 33258 for calculation of apoptotic cells with condensed chromatin. The number of apoptotic cells was determined by counting 100 stained cells in 20 different areas on tissue culture dishes from three independent experiments.

In vitro cell proliferation studies

CU87, T98 or RT2 malignant glioma cells (750/well) were plated onto 96-well plates and allowed to grow for 5–6 days in the presence of the ceramic analogues S16, S18 or B16, or control media. The CellTiter96® Aqueous One cell proliferation assay (Promega, Inc.) was used to quantify glioma cell proliferation. In this assay, the amount of formazan product (490 nm absorbance) made from the conversion of [3-(,5-dimethyl-2-yl)-5-(3-carboxymethoxyphenyl)-2-(4-sulfophenyl)-2H-tetrazolium, inner salt (MTS) by dehydrogenase enzymes of metabolically active cells is directly proportional to the number of living cells in culture.

In vivo tumor model in athymic mice

A total of $1\times10^6$ NG108-15 or F-11 cells in 200 $\mu$l of phosphate buffered saline (PBS) was subcutaneously injected into each side of athymic NU/NU mice (Harlan) for generation of an in vivo brain tumor model in mouse skin. The resulting tumors were treated either intraperitoneally or by direct intratumor injection of ceramic analogs. Tumor growth rates and treatment results were the same within experimental error regardless of whether NG108-15 or F-11 cells were used.

Tumor measurement

Tumor growth was monitored by caliper measurement. The tumor volume was calculated by the formula: tumor size $[mm^3]$=(tumor width $[mm])^2\times$tumor length $[mm]$.

Intraperitoneal treatment

The intraperitoneal administration of ceramic analogs started one day after grafting and was performed twice per day with 0.7 ml of 2 mM S16 or 4 mM S18 corresponding to 50–100 mg/kg per mouse. The compounds were predissolved in dimethylsulfoxide (DMSO) at a maximum concentration of 250 mM and then serially diluted to 2 mM S16 or 4 mM S18 in 20% bovine serum albumin (BSA), 500 $\mu$M sodium stearate, 0.9% sodium chloride.

Intratumoral treatment

The intratumoral administration of ceramic analogs was initiated when tumor size was 30–50 $mm^3$ and consisted of daily injections of a 10-fold concentrated analog solution prepared as described above for S16 or of 2 mM B16 in 0.9% sodium chloride. The final concentration was calculated to be 200 $\mu$M when applied in a volume of 10% of the tumor size. Tumor volume was measured and calculated as described above.

EXAMPLE 1. Alteration of ceramic levels in neuroblastoma cells upon incubation with S16.

NG108-15 or F-11 cells were incubated with 100 $\mu$M S16 overnight and endogenous ceramic analyzed by HPTLC of neutral lipids corresponding to 200 $\mu$g of cellular protein applied per lane. The HPTLC plate was developed in $CHCl_3/HOAc$ (9:1), v/v) and sphingolipids stained with cupric acetate/phosphoric acid reagent. Levels of ceramic, sphingomyelin, and neutral lipids were determined by densitometric analysis and comparison with various amounts of standard lipids. The result showed that there was no detectable alteration of the glycosphingolipid composition or the level of sphingomyelin upon incubation with 100 $\mu$M S16. However, the concentration of ceramic in F-11 and NG108-15 cells at 20% confluence was elevated by about 50–80%. In contrast, incubation of 100% confluent cells showed no significant alteration of endogenous ceramic, indicating that rapidly dividing, but not resting cells, are affected by the presence of S16.

EXAMPLE 2. Dependence of the rate of S16 induced apoptosis on cell density.

Figure 3:
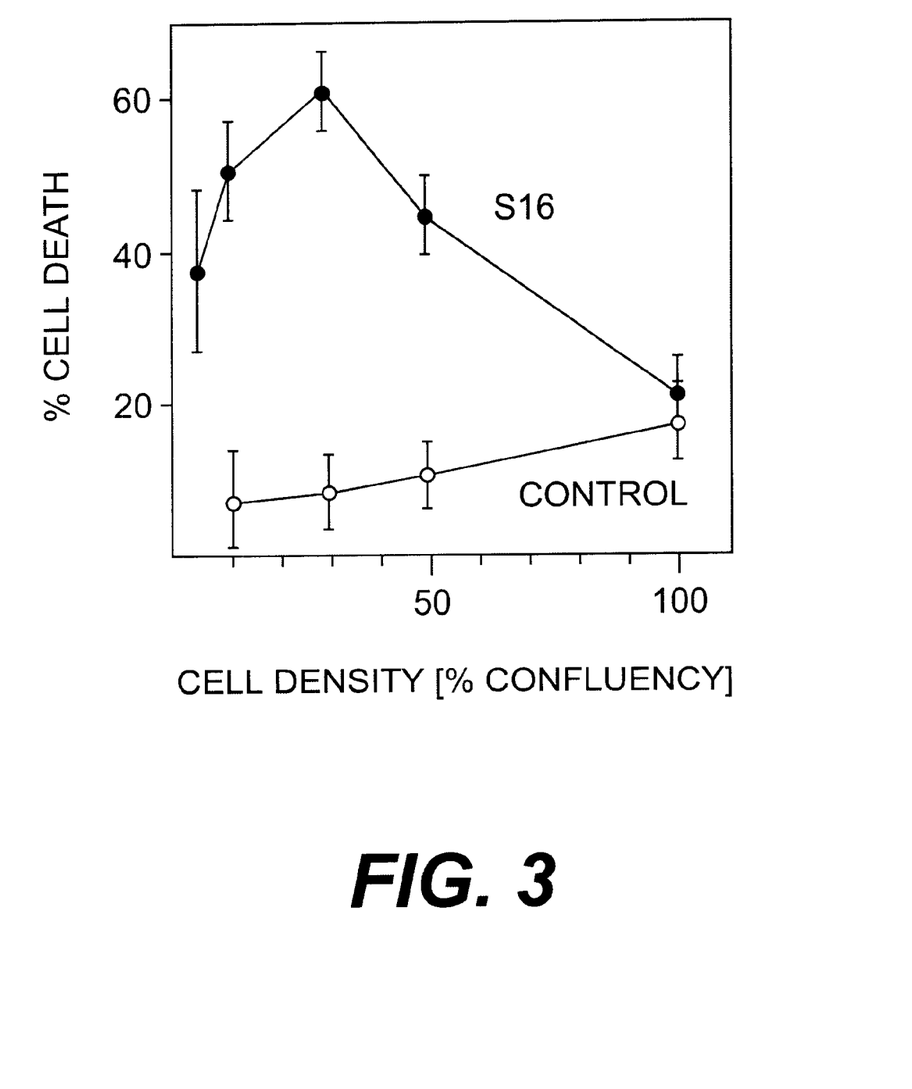
FIG. 3. Dependence of S16 induced apoptosis of NG108-15 cells on cell density. (•) S16; (○) control.

The dependence of the rate of S16 induced apoptosis of NG108-15 cells on cell density was investigated as described in methods and the results are given in FIG. 3. As can be seen, the degree of apoptosis was markedly decreased when the cell density was below 20% or above 50%. This observation was confirmed by determination of cell density-dependent DNA fragmentation (laddering) upon incubation with S16. Cells were incubated with 100 $\mu$M S16 for 15 hours. Those experiments showed that the typical laddering of 200-base pair fragments was increased markedly for 30% confluent cells compared with 100% confluent cells for both NG108-15 and F-11 cells. This observation indicates that the 30% confluent (and therefore rapidly dividing) cells were susceptible to apoptosis by exposure to S16 whereas 100% confluent (resting) cells were not.

EXAMPLE 3. Dependence of apoptosis on cell cycle and cell differentiation.

The dependence of apoptosis on cell cycle was analyzed as described in Methods. Apoptotic cells stained with Hoechst dye or identified by terminal nucleotidyl transferase assay were observed to be concomitantly immunoreactive with anti-cyclin E antibody, indicating that the onset of apoptosis occurred at the G1 to S phase transition.

The apoptotic potential of S16 with respect to cell differentiation was investigated as described in Methods. It was found that only undifferentiated cells showed the typical staining with Hoechst dye after incubation with S16, indicating that undifferentiated, but not differentiated, cells can be induced to undergo apoptosis by exposure to S16.

EXAMPLE 4. Effect of alkyl chain length on apoptotic potential of N-acylated compounds.

Figure 4:
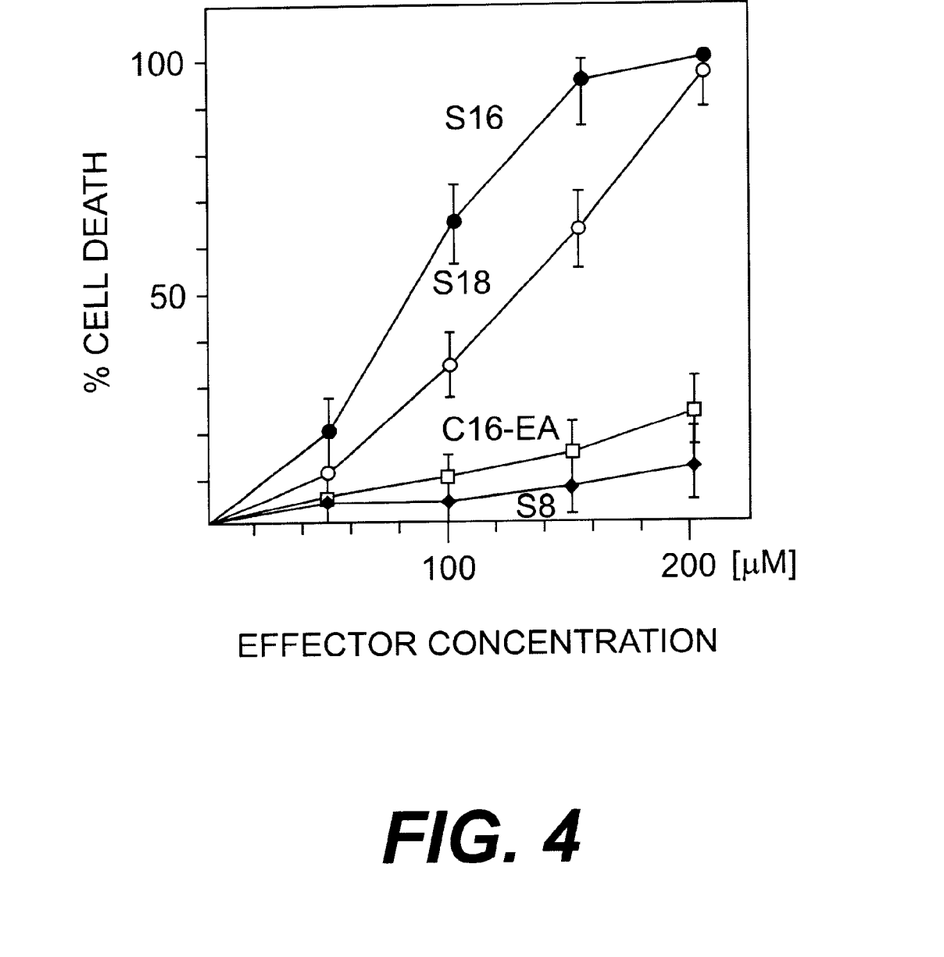
FIG. 4. Apoptosis of neuroblastoma cells and dependence on the alkyl chain length and number of β-hydroxy groups of N-acetylated amides (•) S16; (○) S18; (□) C-16 EA; (♦) S8.

The effect of alkyl chain length on the apoptotic potential of S16 and two compounds differing only in the length of the alkyl chains, S8 (8 carbons)and S18 (18 carbons) was investigated as described in Methods. Also, the contribution of the second β-hydroxymethyl group of S16 was analyzed by comparison with the effect of C16 EA (C16 ethanolamine) on apoptosis. The results are given in FIG. 4. As can be seen, the optimal chain length of the alkyl residue is 16–18. The C8 chain length displayed low apoptotic potential. As such, the preferred length is 12–20 carbons. In addition, almost no apoptosis was observed with C16 EA (C16 ethanolamine), indicating the significance of the second β-hydroxymethyl group of S16.

EXAMPLE 5. Effect of S16, S18, and B16 on proliferation of malignant brain tumor cells in vitro.

Figure 5A:
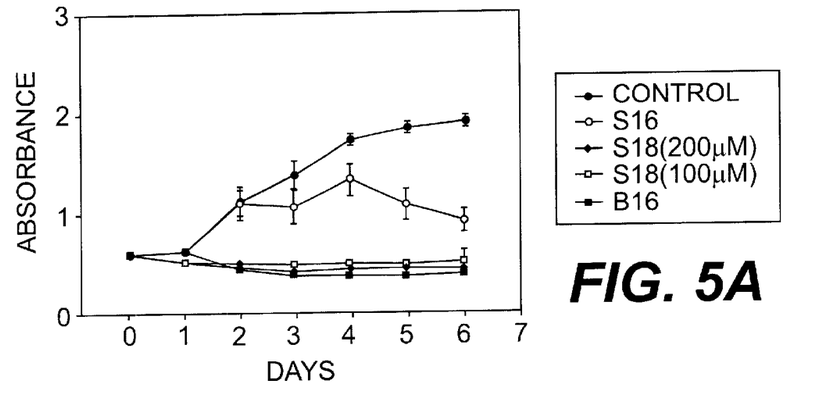
FIGS. 5A, 5B and 5C. MTS proliferation assay of in vitro brain tumor cells (malignant glioma) treated with structural analogues of ceramic. (•) control; (○) S16, 100 μM; (▼) S18, 200 μM; (∇) S18, 100 μM. 5A: U87 cells (6 days); 5B: RT2 cells (6 days); 5C: T98 cells (5 days).
Figure 5B:
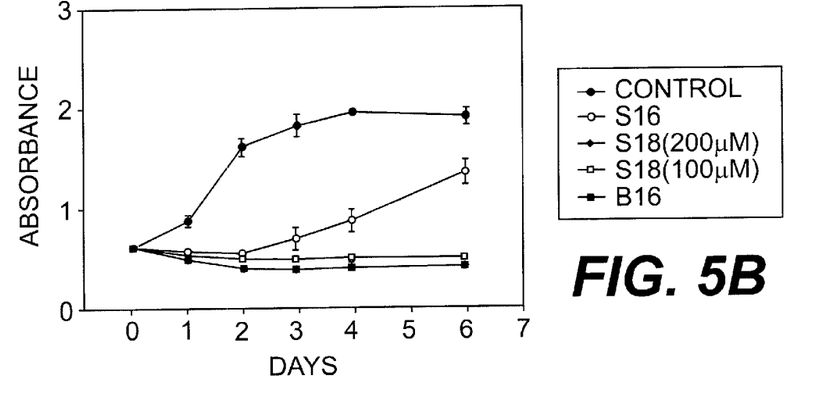
Figure 5C:
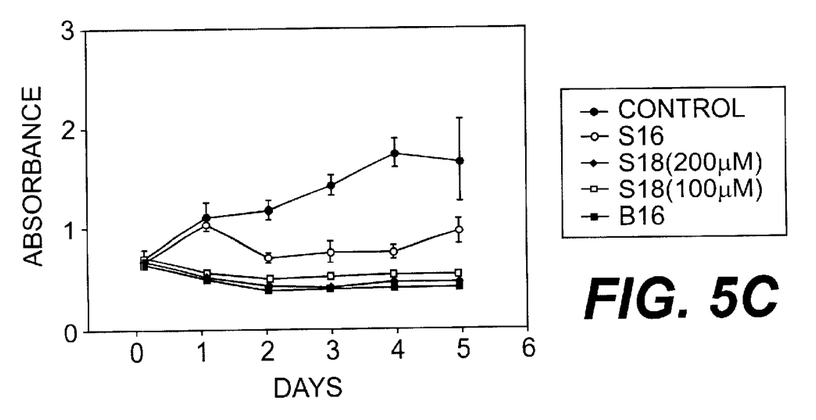

The effect of the compounds S16, S18, and B16 on the ability of U87, RT2 and T98 glioma cells to proliferate in vitro was investigated as described in Methods and the results are presented in FIGS. 5A, 5B and 5C, respectively. As can be seen, for all three cell types, the addition of S16, S18, and B16 resulted in a marked decrease in cellular proliferation. The compounds S18 and B16 appeared to have the most dramatic effect, virtually eliminating the proliferation of all three types of cells.

EXAMPLE 6. Tumor treatment in vivo using S16.

Figure 6:
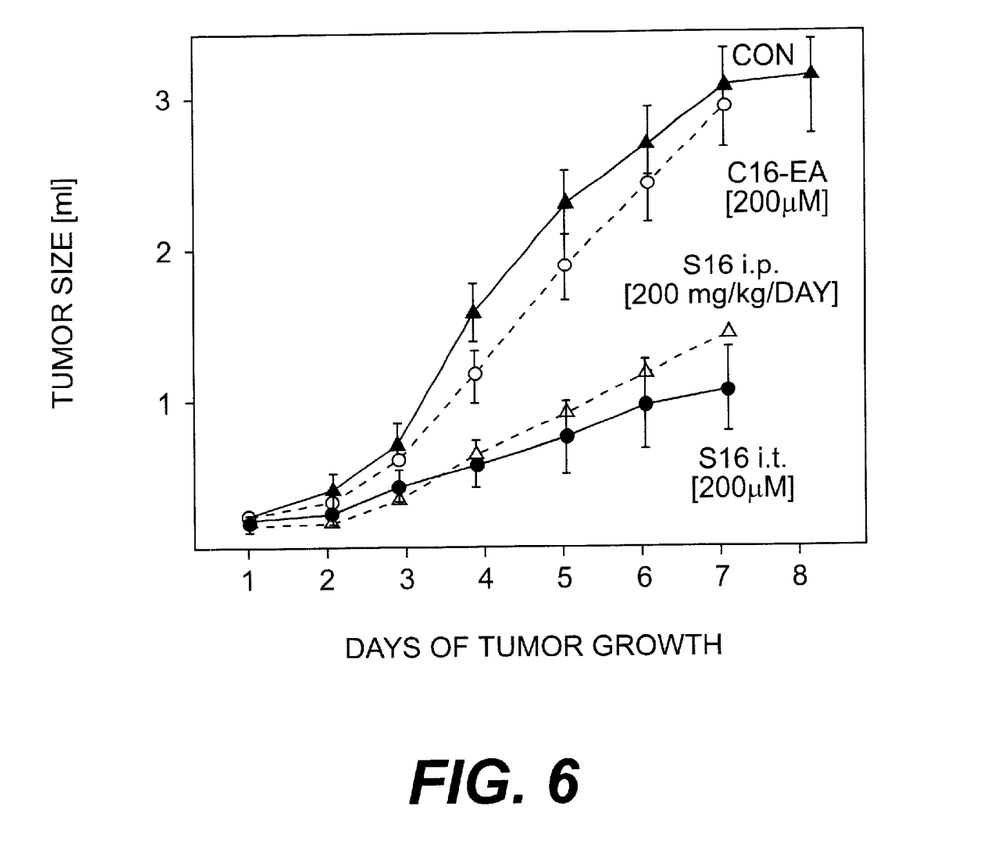
FIG. 6. Treatment of experimentally induced tumors with S16. (•) S16 injected intratumorally; (Δ) S16 injected intraperitoneally; (○) control, treatment with C-16 EA; (▲) control, no treatment.

Athymic mice were grafted with neuroblastoma tumors by subcutaneous injection and treated by intraperitoneal or intratumoral injection of S16 as described in Methods. Control mice received no treatment, or treatment with C-16 EA. The results are given in FIG. 6. As can be seen, the final size of the tumors treated with S16 was only 30–35% of that of untreated or C16-EA treated mice. Furthermore, the first measurable tumors appeared 2 days later in mice treated with S16 than in control mice. No effects of general toxicity were observable even with concentration of up to a total of 200 mg/kg/day of S16 during treatment for 14 days.

EXAMPLE 7. Tumor treatment in vivo with S18 or B16.

Figure 7:
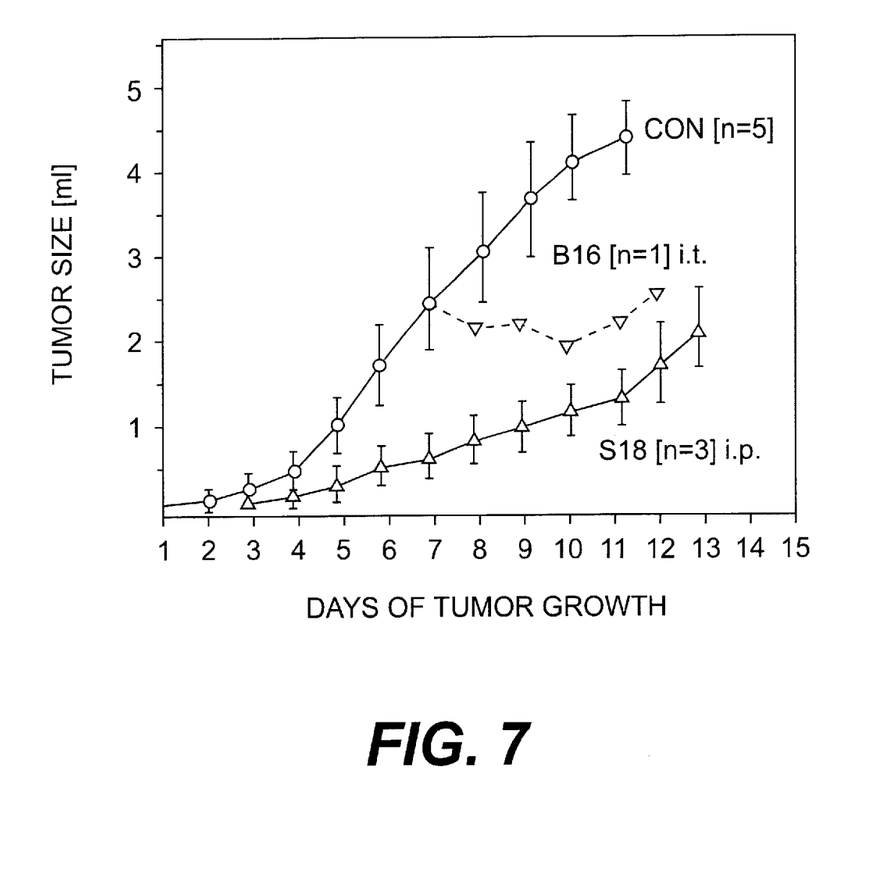
FIG. 7. Treatment of experimentally induced tumors with S18 or B16. (Δ) S18, intraperitoneal injection, n=3; (▽) B16, intratumoral injection, n=1; (○) control, no treatment, n=5.

Athymic mice were grafted with neuroblastoma tumors by subcutaneous injection and the resulting tumors were treated by intraperitoneal injection of S18 or intratumoral injection of B16 as described in Methods. Control mice received no treatment. The results are given in FIG. 7. As can be seen, tumors treated with S18 or B16 were less than 50% the size of tumors in untreated control mice.

EXAMPLE 8. Tumor treatment in vivo with S16 and S18.

Athymic mice were grafted with $1 \times 10^6$ F-11 cells by subcutaneous injection in each side of the mouse.

Figure 8:
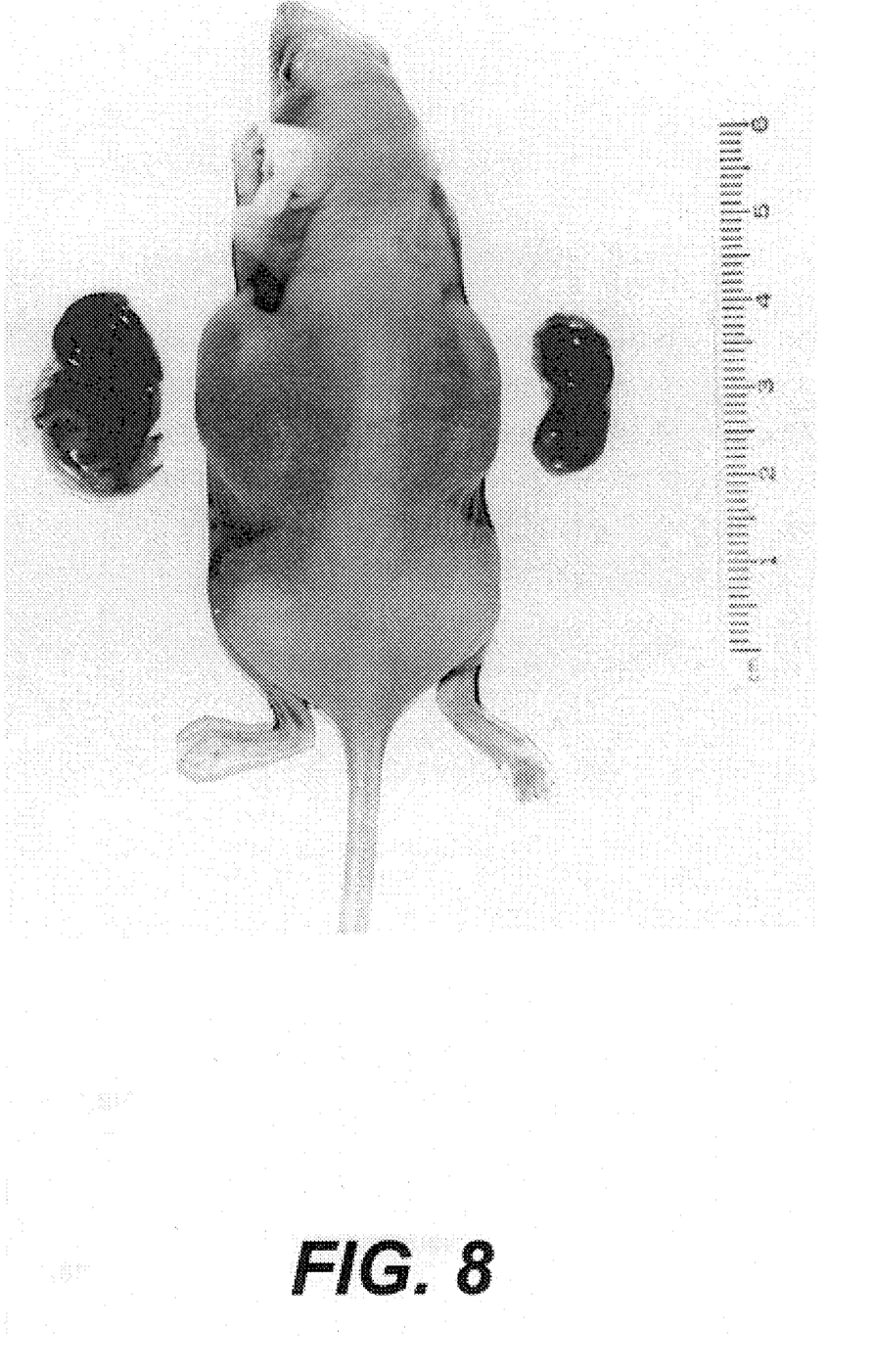
FIG. 8. Results of intra-tumoral administration of S16. Tumor on right side of mouse was treated with intra-tumoral administration of S16; tumor on left side of mouse served as a control and was treated with intra-tumoral administration of C-16 EA.

FIG. 8. The mouse in FIG. 8 was treated daily by intra-tumoral administration (into the tumor on the right side) of 2 mM S16 at a volume equal to 10% of the tumor size at the beginning of treatment. The tumor on the left side was injected with 2 mM N-palmitoyl ethanolamine (C-16 EA) as a negative control.

Figure 9:
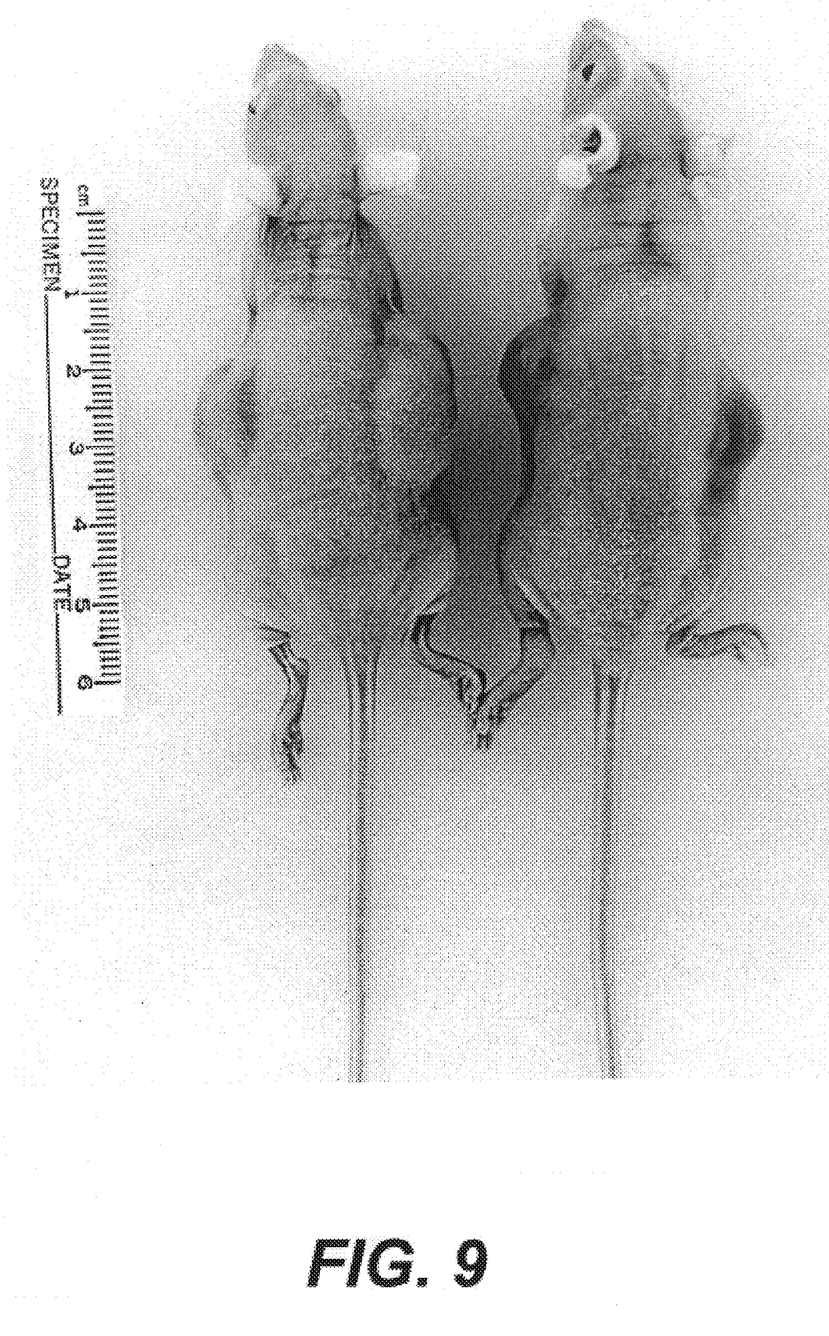
FIG. 9. Results of intra-peritoneal administration of S18. Mouse on the right was treated for 14 days by intra-peritoneal injections of S18. Mouse on the left side was untreated as a negative control.

FIG. 9. The mouse on the right side of FIG. 9 was treated for 14 days by intra-peritoneal injections of 0.7 ml of 4 mM S18 twice a day. The mouse on the left side of FIG. 9 was untreated as a negative control and sacrificed after 10 days. The tumor volume was determined by caliper measurement and was about 4 ml for the mouse on the left side (untreated for 10 days) and 2 ml for the mouse on the right side (treated for 14 days).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Abe et al., (1995) *J. Lipid Res.* 36, 611–621.

Ariga, T., Jarvis, W. D. and Yu, R. K. (1998)

Arora, R. C. and Radin, N. S. (1972) *J. Lipid Res.* 13, 86–91.

Bieberich, E., Freischutz, B., Suzuki, M. and Yu, R. K. (1999) *J. Neurochem.* 72, 1040–1049.

Bieberich, E., Kawaguchi, T. and Yu, R. K. (2000) *J. Biol. Chem.* 275, 177–181.

Bielawska, A., Greenberg, M. S. Perry, D., Jayadev, S., Shayman, J. A., McKay, C., and Hannun, Y. A. (1996) *J. Biol. Chem.* 271, 12646–12654.

Carlin, S., Yang, K. X., Donnelly, R., and Black, J. L.(1999) *Am. J. Physio.* 276, L506–512.

Das, M., Dempsey, E. C., Bouchey, D., Reyland, M. E., and Stenmark, K. R. (2000) *Am. J. Respir. Cell Motil. Biol.* 22, 15–25.

De, B. P., Gupin, S. and Banerjee, A. K. (1995) *Proc. Natl. Acad. Sci. U.S.A.* 92, 5204–5208.

Folgueira, L., McElhinny, J. A., Bren, G. D., MacMorran, W. S., Diaz-Meco, M. T., Moscal, J. and Paya, C. V. (1996) *J. Virol.* 70, 223–231.

Freischutz, B., Tokuda, A., Ariga, T., Bermudez, A. J. and Yu, R. K. (1997) *J. Neurochem.* 68, 2070–2078.

Hannun and Linardic, (1993) *Biochem. Biophys. Acta* 1154, 223–236.

Hochegger, K., Partik, O., Schorkhuber, M, and Marian, B. (1999) *Int. J. Cancer* 83, 650–656.

Huntley, C. C., Bishnu, P. D., Banerjee, A. K. (1997) *J. Biol. Chem.* 272, 16578–16584.

Ji, L., Zhang, G., Uematsu, S., Akahori, Y., and Hirabayashi, Y. (1995) *FEBS Lett.* 358, 211–214.

Jordan, N. J., Watson, M. L., Yoshimura, T., and Westwick, J. (1996) *Br. J. Pharmacol.* 117, 1245–1253.

Macdonald, N. J., Perez-Polo, J. R., Bennett, A. D. and Taglialatela, G. (1999) *J. Neurosci. Res.* 57, 219–226.

Mangoura, D. and Dawson, G. (1998) *J. Neurochem.* 70, 130–138.

Mani, I., Iversen, L., and Ziboh, V. A. (1999) *J. Invest. Dermatol.* 112, 42–48.

Moore, P., White, J., Christiansen, V., and Grammas, P. (1998) *Neurosci. Lett.* 254, 29–32.

Muller G., Ayoub, M., Storz, P., Rennecke, J., Fabbro, D. and Pfizenmaier, K.(1995) *EMBO J.* 14, 1961–1969.1995

Powell, C. T., Geschwend, J. E., Fair, W. R., Brittis, N. J., Stec, D. and Huryk, R. (1996) *Cancer Res.* 56, 4137–4141.

Schwab, M. (1999) *Naturwissenschaften* 86, 71–78.

Ways, D. K., Posekony, K., deVente, J., Garris, T., Chen, J., Hooker, J., Qin, W., Cook, P., Fletcher, D. and Parker, P. (1994) *Cell Growth Differ.* 5, 1195–1203.

We claim:

1. A method for treating inflammation in a patient in need thereof comprising administering to said patient a sufficient quantity of a compound of the general formula wherein

R=a saturated or mono- or polyunsaturated (cis or trans) alkyl group having greater than 5 carbon atoms, R1, R2 and R3 may be the same or different and are hydroxylated alkyl groups, and R4 is hydrogen, an alkyl chain having from 1 to 12 carbon atoms, or an aryl moiety, wherein said administering step causes reduction in inflammation in said patient.

2. A method for inducing apoptosis in cells comprising, exposing said cells to a compound of the general formula wherein

R=a saturated or mono- or polyunsaturated (cis or trans) alkyl group having greater than 5 carbon atoms, R1, R2 and R3 may be the same or different and are hydroxylated alkyl groups, and R4 is hydrogen, an alkyl chain having from 1 to 12 carbon atoms, or an aryl moiety, wherein said exposing step is performed for a time sufficient to induce apoptosis.

3. A method for modulating the activity of the enzyme protein kinase Cζ comprising, exposing said enzyme to a compound of the general formula wherein

R=a saturated or mono- or polyunsaturated (cis or trans) alkyl group having greater than 5 carbon atoms,

R1, R2 and R3 may be the same or different and are hydroxylated alkyl groups, and R4 is hydrogen, an alkyl chain having from 1 to 12 carbon atoms, or an aryl moiety, wherein said compound modulates the activity of said enzyme.

4. A method for treating Alzeimer's in a patient in need thereof comprising administering to said patient a sufficient quantity of a compound of the formula or a compound of the formula wherein said exposing step prevents or reduces the symptoms associated with Alzheimer's disease.

* * * * *